United States Patent [19]

Hyatt et al.

[11] 4,386,221

[45] May 31, 1983

[54] PROCESS FOR THE PREPARATION OF ARYL ALKYL SULFONES AND ARYL VINYL SULFONES

[75] Inventors: John A. Hyatt; Alan W. White, both of Kingsport, Tenn.

[73] Assignee: Eastman Kodak Company, Rochester, N.Y.

[21] Appl. No.: 315,796

[22] Filed: Oct. 28, 1981

[51] Int. Cl.³ .................. C07C 147/06; C07C 147/08
[52] U.S. Cl. ........................................ 568/28; 568/34; 568/35
[58] Field of Search ............................. 568/28, 34, 35

[56] References Cited

FOREIGN PATENT DOCUMENTS 1311218 10/1962 France .................................. 568/28

OTHER PUBLICATIONS

W. E. Truce et al., *J. Amer. Chem. Soc.*, 75, 5032–5036 (1953), Friedl-Crafts Reactions of Methanesulfonyl Chloride with Benzene and Certain Substituted Benzenes.

E. E. Gilbert, *J. Org. Chem.*, 28, 1945 (1963).

L. Field and P. H. Settlage, *J. Amer. Chem. Soc.*, 76, 1222 (1953).

*Primary Examiner*—Donald G. Daus
*Assistant Examiner*—M. C. Eakin
*Attorney, Agent, or Firm*—David E. Cotey; Daniel B. Reece, III

[57] ABSTRACT

The present invention provides a process for the preparation of aryl alkyl sulfones and aryl vinyl sulfones. The process comprises reacting an aryl compound with an alkyl sulfonyl fluoride or with a vinyl sulfonyl fluoride in the presence of a catalyst selected from $AlCl_3$ and $AlBr_3$. The aryl compound is preferably selected from chlorobenzene, the isomeric xylenes, the isomeric trimethyl benzenes, and mixtures thereof. The alkyl group of the alkyl sulfonyl fluoride preferably contains 1–18 carbon atoms, and the vinyl group of the vinyl sulfonyl fluoride is unsubstituted or substituted with one or more alkyl groups containing 1–5 carbon atoms. The reaction is conducted at a temperature between about −25° C. and 150° C. in the presence or absence of an inert solvent.

13 Claims, No Drawings

PROCESS FOR THE PREPARATION OF ARYL ALKYL SULFONES AND ARYL VINYL SULFONES

BACKGROUND OF THE INVENTION

Compounds of the general types aryl—$SO_2$-alkyl and aryl—$SO_2$—C=C (aryl alkyl sulfones and aryl vinyl sulfones) are useful as intermediates and final products in several areas, dyes being especially prominent. Compounds having this structural unit have generally been prepared by way of multistep sequences starting with thiophenols. Little success has previously been achieved in developing direct, one-step methods for the conversion of aryl compounds to aryl sulfones of the types mentioned above.

It is known that Friedel-Crafts reactions of aryl sulfonyl chlorides provide good yields of diaryl sulfones. See, for example, *Friedel-Crafts and Related Reactions*, George A. Olah, Ed., Interscience, New York, 1973. However, the corresponding reaction of alkyl sulfonyl chlorides has usually been reported to give very low yields of the desired sulfone. References which indicate the undesirability of this approach to the preparation of the desired sulfones include E. E. Gilbert, *J. Org. Chem.*, 28, 1945 (1963); L. Field and P. H. Settlage, *J. Amer. Chem. Soc.*, 76, 1222 (1953); and C. M. Suter, *The Chemistry of Sulfur*, John Wiley and Sons, Inc., New York, 1944, pp 673–675.

In an article by W. E. Truce and C. W. Vriesen [*J. Amer. Chem. Soc.*, 75, 5032 (1953)], it is reported that a 70% yield of methyl phenyl sulfone was obtained from methanesulfonyl chloride and benzene using an aluminum trichloride catalyst. However, the reactions of toluene, mesitylene, and halobenzenes with methane sulfonyl chloride in the presence of aluminum trichloride were reported to give only relatively small yields. Likewise, the reaction of p-xylene with methanesulfonyl chloride in the presence of aluminum trichloride has been found by applicants to involve predominantly chlorination of the arene to the virtual exclusion of sulfonylation. Thus, a widely applicable procedure for a direct, one-step conversion of aryl compounds to aryl alkyl sulfones and aryl vinyl sulfones have heretofore not been achieved.

It has now been found, contrary to the expectations of one of ordinary skill in the art, that the desired sulfones can be prepared by the reaction of alkyl and vinyl sulfonyl fluorides with aryl compounds in the presence of aluminum chloride or aluminum bromide catalyst. That is, by replacing alkyl and vinyl sulfonyl chlorides with alkyl and vinyl sulfonyl fluorides, a rapid, convenient, one-step synthesis of aryl alkyl sulfones and aryl vinyl sulfones is achieved. Moreover, the products are provided in yields which are significantly improved over those provided by prior art processes.

The compounds produced by the process of the present invention are useful as intermediates and final products in several areas. For example, certain of the aryl alkyl sulfones are useful as intermediates in the preparation of components for photographic films. The aryl vinyl sulfones are useful as intermediates in the preparation of dyes for wool and polyamide textile products.

SUMMARY OF THE INVENTION

The present invention provides a process for the preparation of sulfones selected from aryl alkyl sulfones and aryl vinyl sulfones. The process comprises reacting one or more aryl compounds of the formula

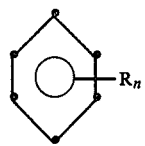

where R represents halogen, alkyl groups containing 1 to 12 carbon atoms, phenyl, and combinations thereof and where n is an integer from 1 to 5, inclusive, with an alkyl sulfonyl fluoride or with a vinyl sulfonyl fluoride in the presence of a catalyst selected from $AlCl_3$ and $AlBr_3$.

DETAILED DESCRIPTION OF THE INVENTION

The present invention relates to a process for the preparation of a selected class of sulfones. Sulfones which are prepared by this method include aryl alkyl sulfones and aryl vinyl sulfones. The process comprises reacting a specified aryl compound with an alkyl sulfonyl fluoride or a vinyl sulfonyl fluoride in the presence of a catalyst selected from aluminum chloride and aluminum bromide.

The aryl compound which may be used as a starting material in the process of the present invention has the formula

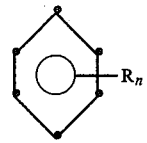

In the above formula, R represents halogen, alkyl groups containing 1–12 carbon atoms, phenyl, and combinations thereof, and n represents an integer from 1–5, inclusive. Thus, the R group in the above formula may be any halogen (i.e., Cl, Br, I, and F), but is preferably chlorine or bromine. The alkyl groups may be straight, branched, or cyclic, and include such groups as methyl, ethyl, n-propyl, isopropyl, n-butyl, iso-butyl, tert-butyl, cyclohexyl, etc. The aryl compound is preferably selected from chlorobenzene, the isomeric xylenes, the isomeric trimethyl benzenes, and mixtures thereof.

In the process of the present invention, the aryl compound described above is reacted with an alkyl sulfonyl fluoride or a vinyl sulfonyl fluoride. The alkyl group of the alkyl sulfonyl fluoride contains 1–18 carbon atoms, inclusive, and may be straight, branched, or cyclic. Thus, the alkyl group may be methyl, ethyl, n-propyl, isopropyl, n-butyl, isobutyl, tert-butyl, cyclohexyl, or even higher alkyl groups, such as those having 10 to 18 carbon atoms (e.g., hexadecyl, heptadecyl, and octadecyl groups). The vinyl group has the structure —CR=CR'R" where R, R', and R" is each independently selected from hydrogen or an alkyl group having 1–5 carbon atoms. Thus, the vinyl group may be unsubstituted or substituted with one or more $C_1$ to $C_5$ alkyl groups.

The reaction of the aryl compound with the alkyl sulfonyl fluoride or vinyl sulfonyl fluoride is conducted in the presence of a Friedel-Crafts catalyst selected from AlCl₃ and AlBr₃. The catalyst is present in an amount of at least about one mole per mole of the alkyl or vinyl sulfonyl fluoride. Preferably, the catalyst is present in an amount of at least about 1.5 mole per mole of alkyl or vinyl sulfonyl fluoride.

The reaction can be conducted in the presence or absence of an inert solvent. Suitable inert solvents which may be employed include methylene chloride, dichloroethane, nitrobenzene, carbon disulfide, etc.

It may be desirable to employ as the solvent in the reaction mixture not an inert solvent such as those described above but an excess of the aromatic compound. It will be apparent to one of ordinary skill in the art that the aromatic compound and the vinyl sulfonyl fluoride or alkyl sulfonyl fluoride will react in a 1:1 molar ratio. Any excess of a suitable aromatic compound will therefore serve as a solvent in the reaction mixture. Thus, it may be desirable to employ a molar ratio of aromatic compound:sulfonyl fluoride of approximately 3:1 to 10:1 or higher.

The reaction is conducted at a temperature between about −25° C. and 150° C. The temperature which is most desirably employed in a particular process will depend upon the reactivity of the specific reactants which are employed. Thus, it is desirable to employ a higher temperature when the aryl compound contains a chloro substituent (a less reactive compound) than when the aryl compound contains one or more lower alkyl substituents (a relatively more reactive compound). Preferably, the reaction is conducted at a temperature within the range of about 0°–125° C. and, more preferably, within the range of about 25°–100° C.

The alkyl sulfonyl fluorides and vinyl sulfonyl fluorides which are employed as reactants in the process of the present invention are obtainable in laboratory quantities from such sources as the Eastman Kodak Company and the Aldrich Chemical Company. The alkyl or vinyl sulfonyl fluorides may also easily be prepared by known methods from the corresponding sulfonyl chlorides. Briefly, the sulfonyl chloride is reacted with potassium fluoride in the presence of water to produce the corresponding sulfonyl fluoride. This preparative procedure is easily practiced by one of ordinary skill in the art.

It is desirable that the reaction temperature be chosen so that the reaction proceeds at a reasonable rate. Preferably, the reaction is complete within a period of time of approximately 0.5–10 hours, e.g., within a time of about 1–5 hours.

The use of sulfonyl fluorides, instead of sulfonyl chlorides, is essential to the process of the present invention. While not wishing to be bound by theoretical considerations, it appears that when alkyl sulfonyl chlorides react with aromatic hydrocarbons in the presence of aluminum chloride, the major reaction which occurs is chlorination, not sulfonylation, of the aromatic compound. For example, the reaction of p-xylene with methanesulfonyl chloride in the presence of aluminum chloride gave a 70% yield of 2,5-dimethylchlorobenzene and less than 1% yield of 2,5-dimethylphenyl methyl sulfone, as shown below:

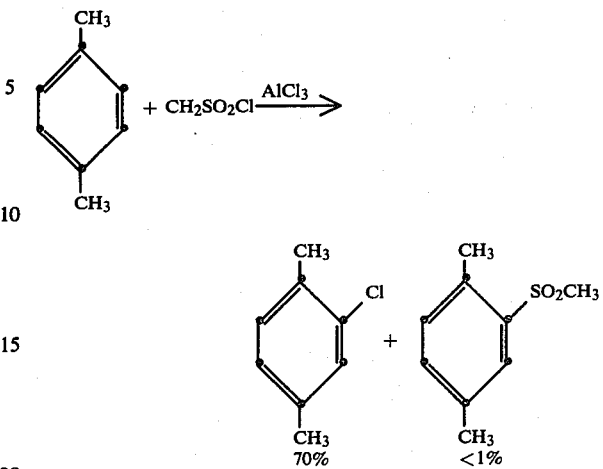

The corresponding chlorination reaction was found to occur with toluene, xylenes, and mesitylene, often to the virtual exclusion of sulfonylation. This undesired chlorination reaction accounts for the low yields previously reported in attempted alkyl sulfonyl chloride Friedel-Crafts reactions.

A possible explanation for this phenomenon is that the sulfonyl chloride and aluminum chloride could interact in two different ways:

1. $R-SO_2Cl + AlCl_3 \rightleftharpoons [R-SO_2^+ AlCl_4^-]$
2. $R-SO_2Cl + AlCl_3 \rightleftharpoons [Cl^+ RSO_2AlCl_3^-]$ Pathway 1 leads to an electrophilic sulfur species which, upon reaction with an aromatic compound, would give the desired sulfone product; pathway 2 gives electrophilic chlorine, which would lead to ring chlorination of the aromatic compound. The latter pathway appears to predominate in the prior art reactions described above.

It now appears that, by replacing $R-SO_2Cl$ with $R-SO_2F$, pathway 2 is suppressed, the high electronegativity of F retarding formation of electrophilic $F^+$. Indeed, when p-xylene was reacted with methanesulfonyl fluoride and AlCl₃, the desired sulfone was produced in 91% yield; no fluorinated xylene was observed.

Thus, the reaction of alkyl and vinyl sulfonyl fluorides with an aromatic compound in the presence of AlCl₃ or AlBr₃ catalyst provides a rapid, convenient, one-step synthesis of aryl alkyl and aryl vinyl sulfones.

These compounds find utility as intermediates and final products in several areas. The aryl alkyl sulfones are useful as intermediates in the preparation of components for photographic film. Those aryl alkyl sulfones containing relatively long carbon chains (e.g., 10–18 carbon atoms) can be used, for example, as "ballast" in order to prevent gelling in compositions used in the production of photographic film. The aryl vinyl sulfones are useful as intermediates in the preparation of dyes for wool and polyamide textile products.

This invention will be further illustrated by the following Examples although it will be understood that these Examples are included merely for purposes of illustration and are not intended to limit the scope of the invention.

EXAMPLE 1

This Example illustrates the preparation of 2,5-dimethylphenyl methyl sulfone by the process of the present invention.

To a solution of 2.0 g (0.02 mole) of methanesulfonyl fluoride and 20 ml of p-xylene (0.16 mole) was added 4.0 g of AlCl$_3$ (0.03 mole) in portions over a period of five minutes. During the addition, the temperature rose to 50° C., and gas was evolved. After the reaction mixture had stirred for one hour, it was poured into ice water and extracted with CHCl$_3$. The organic phase was dried and concentrated to provide a colorless liquid which was evaporatively distilled at 0.1 mm and about 120° C. The desired sulfone was obtained as a colorless, viscous oil in 91% yield (3.35 g). The structure of the product was confirmed by NMR, IR, and mass spectroscopy.

COMPARATIVE EXAMPLE 1

This Comparative Example illustrates the undesirable results obtained using a prior art process.

A mixture of 2.3 g (0.02 mole) of methanesulfonyl chloride, 20 ml (0.16 mole) of p-xylene, and 3.1 g (0.023 mole) of AlCl$_3$ was stirred for one hour at 25° C. The product was worked up as described above in Example 1. 2,5-dimethylchlorobenzene was obtained in a 70% yield. NMR and VPC analysis of the crude product showed the presence of less than 1% of 2,5-dimethylphenyl methyl sulfone.

EXAMPLE 2

This Example illustrates the preparation of n-butyl-2,5-dimethylphenyl sulfone by the process of the present invention.

Using the procedure described in Example 1, n-butyl sulfonyl fluoride and p-xylene were reacted in the presence of aluminum chloride. Evaporative distillation of the product at 0.5 mm and 140°–160° C. provided 3.95 g (87% yield) of the desired sulfone as a viscous, colorless oil. The structure of the product was confirmed by NMR, IR, and mass spectroscopy.

EXAMPLE 3

This Example illustrates the preparation of 2,5-dimethylphenyl hexadecyl sulfone by the process of the present invention.

A mixture of 17.0 g of 1-hexadecanesulfonyl chloride, 12 g of potassium fluoride, 15 ml of water, and 50 ml of tetrahydrofuran was refluxed for 30 hours. The mixture was diluted with water, extracted with ether, and dried over magnesium sulfate. The crude product was recrystallized from hexanes at low temperature. The product exhibited a melting point of 42°–43° C. The yield was 15.2 g (97%). The structure of the resulting 1-hexadecanesulfonyl fluoride was confirmed by NMR, IR, and mass spectroscopy.

To a solution of the 1-hexadecanesulfonyl fluoride so produced (6.46 g, 0.02 mole) in 20 ml of p-xylene (0.16 mole) was added 4.0 g of AlCl$_3$ (0.03 mole) at room temperature. After a mild exotherm had subsided, the reaction mixture was stirred for five hours at room temperature. The work-up was the same as described previously. The crude material was obtained in a yield of 8.0 g (86%). Recrystallization from hexanes at low temperature provided 5.6 g of the desired sulfone which exhibited a melting point of 49°–50° C. The structure of the sulfone was confirmed by NMR, IR, and mass spectroscopy.

EXAMPLE 4

This Example illustrates the preparation of 2,5-dimethylphenyl vinyl sulfone by the process of the present invention.

14.7 g (0.11 mole) of AlCl$_3$ was added in portions to a solution of 14 g of p-xylene (0.13 mole) and 10.5 g of vinyl sulfonyl fluoride (0.095 mole) in 100 ml of 1,2-dichloroethane at −10° C. After having been stirred for three hours at room temperature, the solution was poured into ice water. The usual work-up was followed by Kugelrohr distillation to provide the desired sulfone in 79% yield (14.8 g). Recrystallization from a mixture of hexanes and ethyl acetate gave white crystals having a melting point of 48°–50° C. The structure of the sulfone was confirmed by NMR, IR and mass spectroscopy.

EXAMPLE 5

This Example illustrates the preparation of 2,4,6-trimethylphenyl methyl sulfone by the process of the present invention.

To a solution of 2.0 g of methanesulfonyl fluoride (0.02 mole) and 10 ml of mesitylene (0.072 mole) was added 2.70 g of AlCl$_3$ (0.2 mole). After having been stirred for 30 minutes, the solution was poured into ice water and was subjected to the usual work-up. The yield of product was 2.74 g (70%). The product exhibited a melting point of 130° C. The structure of the product was confirmed by NMR, IR, and mass spectroscopy.

EXAMPLE 6

This Example illustrates the preparation of chlorophenyl methyl sulfone by the process of the present invention.

To a solution of methanesulfonyl fluoride (2.0 g, 0.02 mole) in 20 ml of chlorobenzene (0.2 mole) was added 4.0 g of aluminum chloride (0.3 mole). The resulting solution was heated to 110° C. for two hours. After the solution had cooled, it was poured into ice and extracted with chloroform. The crude product was obtained in a yield of 30.4 g (89%). Analysis by NMR indicated that the product was a mixture of isomers (3:1 para:meta). Recrystallization from a mixture of hexanes and chloroform provided a product which was approximately 90% p-chlorophenyl methyl sulfone.

Although the invention has been described in detail with particular reference to preferred embodiments thereof, it will be understood that variations and modifications can be effected within the spirit and scope of the invention.

We claim:

1. A process for the preparation of sulfones selected from aryl alkyl sulfones and aryl vinyl sulfones, said process comprising reacting one or more aryl compounds of the formula

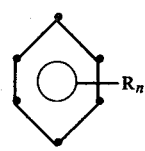

where R represents alkyl groups containing 1 to 12 carbon atoms and combinations thereof and where n is an integer from 1 to 5, inclusive, with an alkyl sulfonyl fluoride or with a vinyl sulfonyl fluoride in the presence of a catalyst selected from AlCl$_3$ and AlBr$_3$.

2. The process of claim 1 wherein said catalyst is present in an amount of at least about 1 mole per mole of said alkyl or vinyl sulfonyl fluoride.

3. The process of claim 1 wherein said catalyst is present in an amount of at least about 1.5 mole per mole of said alkyl or vinyl sulfonyl fluoride.

4. The process of claim 1 wherein the alkyl group of said alkyl sulfonyl fluoride contains 1 to 18 carbon atoms.

5. The process of claim 1 wherein the alkyl group of said alkyl sulfonyl fluoride is methyl.

6. The process of claim 1 wherein the alkyl group of said alkyl sulfonyl fluoride contains 10 to 18 carbon atoms.

7. The process of claim 1 wherein said aryl compound is selected from the isomeric xylenes, the isomeric trimethyl benzenes, and mixtures thereof.

8. The process of claim 1 wherein the vinyl group of said vinyl sulfonyl fluoride is unsubstituted or substituted with one or more alkyl groups containing 1 to 5 carbon atoms.

9. A process for the preparation of sulfones selected from aryl alkyl sulfones and aryl vinyl sulfones, said process comprising reacting one or more aryl compounds of the formula

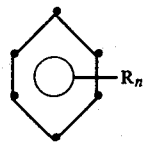

where R represents alkyl groups containing 1 to 12 carbon atoms and combinations thereof and where n is an integer from 1 to 5, inclusive, with an alkyl sulfonyl fluoride, the alkyl group thereof containing 1 to 18 carbon atoms, or with a vinyl sulfonyl fluoride, the vinyl group thereof being unsubstituted or substituted with one or more alkyl groups containing 1 to 5 carbon atoms, in the presence of a catalyst selected from AlCl$_3$ and AlBr$_3$, said catalyst being present in an amount of at least about one mole per mole of said alkyl or vinyl sulfonyl fluoride.

10. The process of claim 9 wherein said catalyst is present in an amount of at least about 1.5 mole per mole of said alkyl or vinyl sulfonyl fluoride.

11. The process of claim 9 wherein the alkyl group of said alkyl sulfonyl fluoride is methyl.

12. The process of claim 9 wherein the alkyl group of said alkyl sulfonyl fluoride contains 10 to 18 carbon atoms.

13. The process of claim 9 wherein said aryl compound is selected from the isomeric xylenes, the isomeric trimethyl benzenes, and mixtures thereof.

* * * * *